United States Patent

Drennan et al.

[11] 4,195,047
[45] Mar. 25, 1980

[54] METHOD FOR REPAIRING BROKEN DENTURE

[76] Inventors: Herman R. Drennan, 32888 Palomares Rd., Castro Valley, Calif. 94546; Norman A. Hana, 5520 Longview Dr., Paradise, Calif. 95969

[21] Appl. No.: 899,293

[22] Filed: Apr. 24, 1978

Related U.S. Application Data

[62] Division of Ser. No. 731,282, Oct. 12, 1976, abandoned.

[51] Int. Cl.² .......................... A61C 13/04; B29C 5/00; B29D 9/00
[52] U.S. Cl. ......................................... 264/17; 264/36; 264/157; 264/219; 264/222; 264/225; 264/255; 264/261; 264/313; 264/338; 433/167
[58] Field of Search .................................... 264/16–18, 264/36, 219, 220, 225, 250, 261, 138, 157, 313, 255, 222, 338, 267; 32/2, 15; 106/38.5 D

[56] References Cited

U.S. PATENT DOCUMENTS

| | | | |
|---|---|---|---|
| 4,017,971 | 4/1977 | Hazar | 32/2 |
| 4,080,412 | 3/1978 | Colpitts et al. | 264/17 |
| 4,094,067 | 6/1978 | Hazar | 32/2 |

*Primary Examiner*—W. E. Hoag
*Attorney, Agent, or Firm*—Joseph L. Strabala

[57] ABSTRACT

Using a highly flowable silicone putty which can be combined with catalysts to set, dentures can be repaired and modified by flowing the putty onto the dentures, allowing it to set while in intimate contact therewith, removing the dentures from the set putty for effecting changes, and subsequently reinserting the dentures in the set putty to effect any necessary changes, modifications or repairs. Prior art practices often used dental stone which had to be chipped away from the dentures when effecting repair or modification. Methods of repairing and modifying dentures herein described involve the steps of forming a flowable mass of moldable, settable silicone putty which has been mixed with a catalyst to cause it to progressively set, molding said putty to a denture surface and allowing it to set while in intimate contact with said denture, thereafter extracting said denture from said putty by flexing the latter, effecting the necessary changes to said denture and subsequently replacing said denture in said set putty by flexing the latter to obtain the proper positioning thereof for effecting any necessary changes and repairs.

2 Claims, 5 Drawing Figures

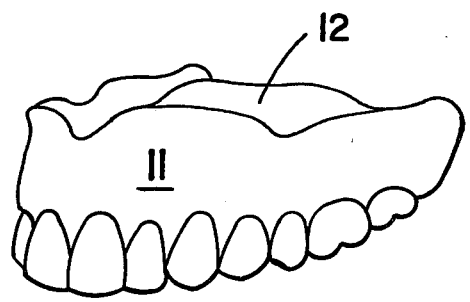
FIG_1
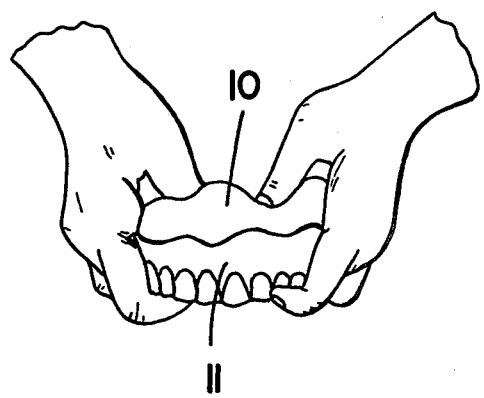
FIG_2
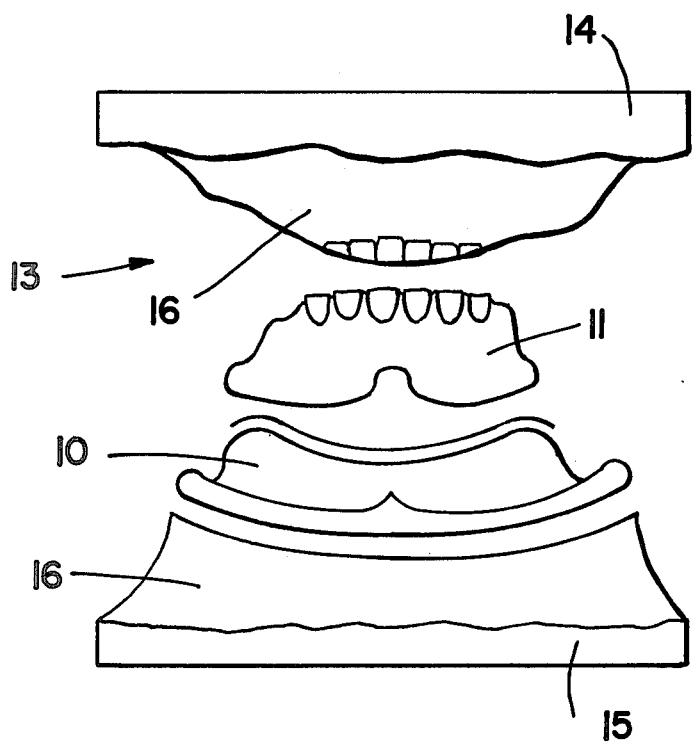
FIG_3

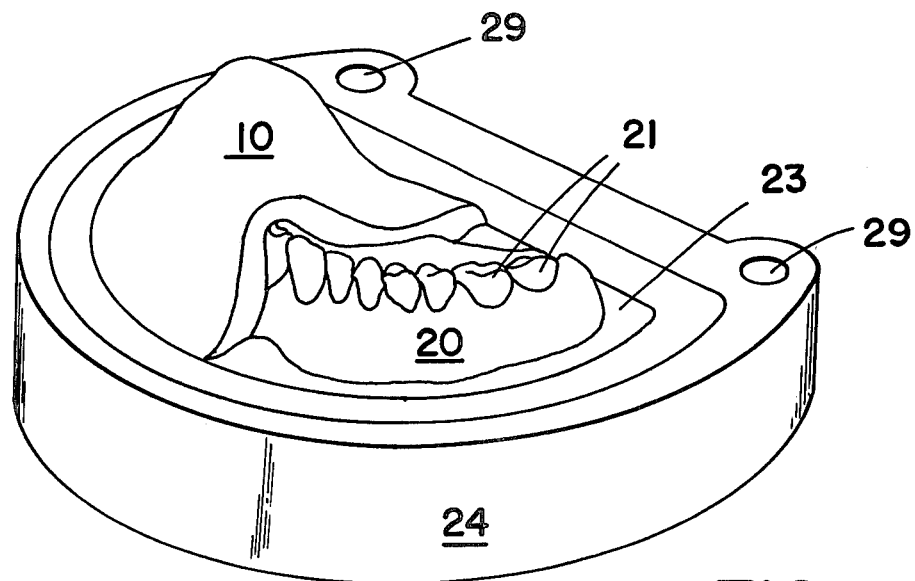
FIG_4
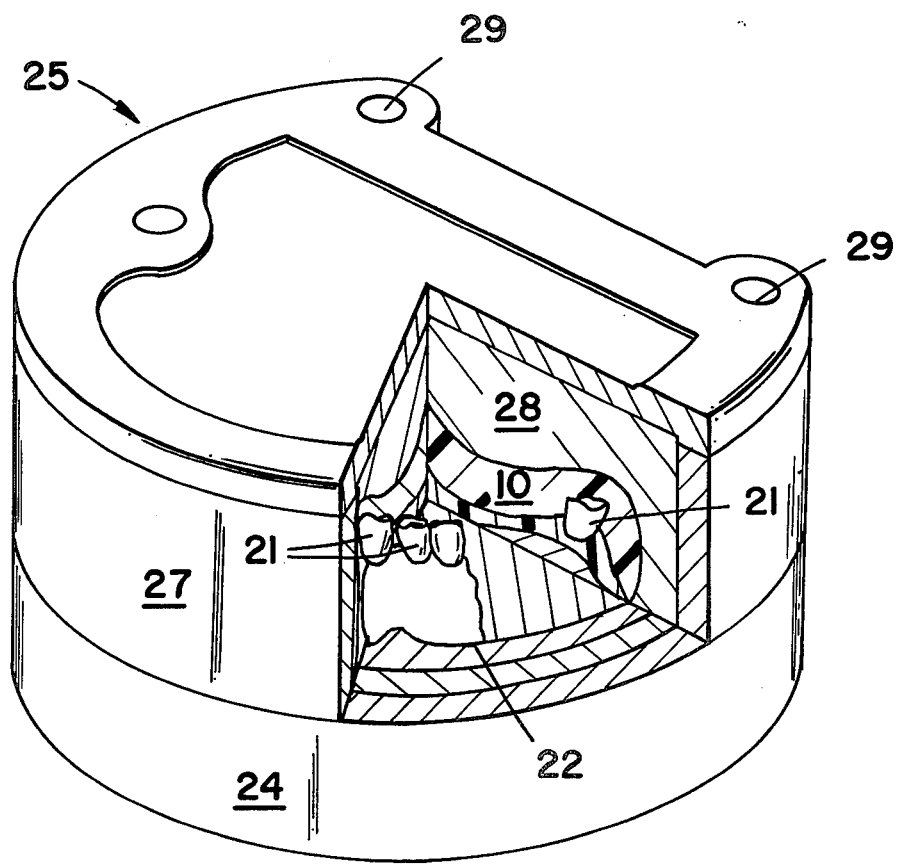
FIG_5

METHOD FOR REPAIRING BROKEN DENTURE

This is a division of Ser. No. 731,282, filed Oct. 12, 1976, now abandoned.

BACKGROUND OF THE INVENTION

This invention relates to a novel molding composition, a method for its preparation and its use in the manufacture and repair of dentures and the taking of dentate impressions. More particularly it relates to a settable laboratory putty.

The use in the dental field of molding compositions such as settable thiol polymers, silicone rubber polymers, cementious compositions and the like is known. This use, in general, is subject to drawbacks and inconveniences. For example, molding compositions containing thiol polymers are usually malodorous and, like conventional molding materials prepared from silicone rubber precursors, their use in denture work involves premixing of a tacky liquid with a suitable setting catalyst using a spatula or the like. Undesirable sticking of mold components to denture components in denture manufacture and repair often makes necessary undercutting and chipping away of adhering molding composition, for example cement, from the denture. Conventional practice includes introduction in a denture mold of spillways for the withdrawal of excess acrylic or epoxy denture-forming compositions. These spillways, vents, etc. leave spurs, ridges and the like in the shaped denture which must be removed in a manner providing at least a reasonable fit for the wearer in that area. These operations all increase the cost and time involved in the manufacture and/or repair of a denture, and the quick facile production of a perfectly fitting denture is, more often than not, the exception rather than the rule.

It is an object of this invention to provide a settable molding composition suitable for use in the manufacture, or repair of a denture which (1) can be effectively used in connection with wax impressions and cementious solids and denture components without problems of undesirable adhesion or the use of spacer materials and the like, (2) does not require the introduction of spillways, vents and the like for the flushing of excess denture-forming materials, epoxy or acrylate resins or the like, from a mold prepared therefrom, (3) results in the production of a true fitting denture without the grinding, buffing, etc. normally involved in removing spurs, ridges and the like produced by spillways or vents in a denture mold, and (4) may be conveniently and directly combined with a suitable setting catalyst by hand kneading the catalyst into the composition without intermediate spatulation or the like. These and other objectives and the satisfaction thereof will be clear from the examples and descriptions to follow.

SUMMARY OF THE INVENTION

This invention is a settable and moldable composition which is suitable for use in denture manufacture and repair comprising:

(1) a lubricating component containing in about equal parts by weight a paraffinic mineral oil having a viscosity in the range from about 170 to 350 cs., preferably near 350 cs., and a silicone oil having a viscosity in the range from about 10K to 100K cs., preferably 60K cs.;

(2) a filling component comprising at least one material selected from the group consisting of the oxides, carbonates and sulfates of the alkaline earths of Group II, preferably calcium carbonate, said material being sized in the average diameter range 5 to 20 microns but below about 75 microns, preferably 80% under 10 microns and sized to pass through a U.S. 325 sieve screen;

(3) at least one pacifying component selected from the group consisting of tetra lower alkyl orthosilicates, preferably tetra ethyl orthosilicate, and (4) a binding component selected from the group consisting of RTV (room temperature vulcanizable) silicone rubber precursors;

said composition containing by weight for each 100 parts of the filling component an amount (1) of the lubricating component in the range 12 to 28 parts, preferably 16 to 20, (2) of the pacifying component in the range 0.4 to 1.6 parts, preferably 0.6 to 1.4 and (3) of the binding component in the range 4 to 12 parts, preferably 6 to 10.

In a further aspect of the invention the above composition is prepared by a method comprising:

(1) producing an emulsion by admixing the aforementioned lubricating and pacifying components;

(2) admixing incrementally the filling component to the emulsion; and (3) admixing the binding component to the resulting mixture from (2) above.

In a yet further aspect of the invention the settable composition above is used to produce a mold or impression of at least a portion of a denture or dentate (i.e., gums, pallate and the like) surface in a method comprising:

(1) producing a setting mixture of the aforementioned composition by hand kneading therein an amount of an RTV silicone polymerization catalyst sufficient to produce a set thereof, for example having a Shore A durometric hardness value in the range 40 to 70, preferably about 55, within a period of about 2 to 30 minutes;

(2) prior to the set, pressing by hand the setting mixture into continuing intimate contact with the portion of denture or dentate surface, thereby applying a coating of the mixture over the surface, said coating having a thickness in the range from about 25 mils to one-quarter inch, preferably about three-eights to one-quarter inch; and (3) after the passing of said setting time and the completion of the set, removing the resulting mold or impression from said denture or dentate surface.

DESCRIPTION OF THE DRAWINGS

The process portion of the invention herein can be better understood by reference to the drawings wherein:

FIG. 1 is a front perspective of a denture with a wash applied to the pallate to facilitate a reline operation;

FIG. 2 is a front elevation of the denture shown in FIG. 1 showing the new putty hand-formed over the wash on the pallate to generate an accurate impression;

FIG. 3 illustrates in exploded elevation a jig arrangement for completing the reline operation after the wash has been removed from the pallate with both the cured putty and dentures invested in dental stone in the two halves of the jig;

FIG. 4 is a perspective with parts broken away, illustrating a wax model set with teeth invested in dental stone in a lower half of a flask with the new putty formed directly over the teeth and roof pallate; and FIG. 5 is a broken-away perspective of both halves of a flask assembled for forming dentures from acrylic materials.

EMBODIMENT

In a preferred embodiment the composition herein contains (1) a lubricating component which is heavy mineral oil plus a silicone oil which has a viscosity of 60,000 cs. (60K), (2) tetra ethyl orthosilicate, (3) calcium carbonate particles sized to pass a U.S. 325 mesh screen, and (4) a silicone rubber precursor obtained by thoroughly mixing in the following weight ratio (1) 55 parts of a heavy mineral oil (for example, a commercial grade mineral oil having a viscosity of about 18 cs.), (2) 60 parts of silicone oil having a 60K viscosity, for example dimethyl-polysiloxane, and (3) 5parts of tetra ethyl orthosilicate, thereby producing an emulsion. Then 600 parts of finely divided calcium, carbonate, essentially all of which passes a U.S. 325 mesh sieve screen, is added with efficient stirring incrementally, 75 percent (450 parts) in a first portion and the balance in smaller amounts at a rate in which, from visual appearances, the added materials is promptly "wet" by the liquid in the emulsion. Preferably the mixing during the carbonate addition is effected by means of a high shear mixer, the mixing being continued until small relatively uniform balls or pills of the resulting mix are formed. These ordinarily have a diameter of about 0.01 to 0.05 inches, usually about 0.02 inches. Thereafter, a suitable RTV rubber precursor, for example a commercial material such as the composition of the General Electric Co. known as RTV-11 or that of the Dow Corning Co. known as Dow 3110 (these materials usually contain about 35 weight percent of micronized calcium carbonate), is admixed in an amount of about 80 parts into the balled or pilled material prepared as described above. The resulting composition should be essentially free of air and voids. To this end, the final mixing step is effected under subatmospheric conditions or the resulting mix is prepared under ordinary conditions and is degassed by a subsequent vacuum degassing treatment. The composition of the invention should be essentially free of air spaces because such spaces may be the source of surface imperfections, bumps, ridges and the like on surfaces of a denture prepared using the composition and method herein.

In this embodiment the above described settable composition is used in the layer molding method for the preparation of a denture; for example in a flasking operation using a standard Hanau flask for acrylic or epoxy dentures, or a Jectron or Luxene flask for thermo-plastic denture materials. The waxed-up denture on the master model is invested in the lower half of the denture flask in the customary manner. About 1-2 cubic inches of the settable composition is converted to a setting composition by kneading by hand an appropriate amount of a conventional RTV setting catalyst, for example stannous octoate, or the like, into the composition. The setting of the compositin ensues promptly and is complete in from about 2 to 30 minutes depending (1) upon the particular catalyst used and (2) the relative amount of the catalyst used. On the basis of the amount by weight of the RTV silicone rubber precursor present in the kneaded material, an amount of the catalyst in the range from about 0.3 to 1 weight percent is, in general, satisfactory. Where a commercially available catalyst is used (such as a std. 33% solution), a satisfactory amount is usually in the range of from about 5 to 30 drops thereof. As the kneading of the catalyst into the settable composition is carried on, the viscosity of the mix gradually increases and is conveniently sensed by the "hand feel" thereof. Before the setting is completed and while the mix is workable, it is spread by hand over all of the surface of a waxed-up denture in a layer which is of the desired thickness, for example about three-eighths of an inch thick.

When the mixture of catalyst and settable composition has substantially set, that is no longer deforms under moderate finger pressure, the remaining void volume in the flask is filled with dental stone, flasking plaster or the like cementious material.

The next step, the boiling out, is carried out in the customary manner. The opened flask is flushed out with hot or boiling water and allowed to cool. At this stage, each tooth formerly embedded in the wax of the waxed-up denture is firmly held or seated in the molded and set composition herein.

An especial advantage of the present material relative to conventional materials is that spillways, vents or the like are not required to relieve the internal pressure during trial packing on those materials requiring it, for example acrylic and epoxy resins and the like. The impressions or molds prepared from the instant compositions exhibit a minor yet effective degree of flexibility to permit flasking of any packing material in excess of the amount required for complete filing of the mold without risk of distorting the mold or of displacing the embedded teeth from the desired position.

The remainder of the procedure follows conventional practice except that the burring and grinding away of protruding bumps, ridges, spurs and the like caused by conventional spillways is wholly unnecessary. The molded composition herein readily releases without permanent deformation from the denture material and the teeth, with no adherence to this composition of flasking stone, plaster or the like. The task of chipping plaster away from the teeth is eliminated with a consequent material reduction in the finishing steps, including polishing and the like. The resulting dentures, in general, fit better and have an improved appearance relative to a denture prepared by conventional means.

The composition herein is useful for the preparation of impressions and molds of all or a portion of dentures and dentate surfaces, gums, pallate, teeth and the like and such use is contemplated.

The Lubricating Component

The lubricating component and the relative amount present in the composition herein may vary widely depending in the main upon the filler component and upon the particular RTV silicone rubber precursor employed. In general a satisfactory composition is obtained when (1) the paraffinic mineral oil has a viscosity in the range from about 2 to 22, preferably about 18 cs. (2) the silicone oil has a viscosity in the range from about 10K to 100K cs., preferably about 60K and (3) for each part by weight of mineral oil the lubricant contains an amount of silicone oil in the range from about 0.8 to 1.2 parts, preferably about 1.1 parts. For each 100 parts (weight) of fillirg component the composition herein should contain an amount of lubricating component in the range 12 to 28 parts, preferably 16 to 20 parts. Representative silicone oils include polymethylsiloxane, such as Dow Corning 200 fluid.

The Filling Component

The filling component may vary widely. It should be essentially insoluble in hot water, for example exhibit a solubility in water at temperatures up to about 100° C.

which is of the order of the solubility of calcium carbonate at that temperature. A low water solubility is desirable in order to avoid the risk of pitting of the set composition in a mold or impression, for example during hot water flushing out of a flask during layer molding of a denture or the like. Satisfactory filling components are in general sized in the average diameter range below about 10 to 20 microns, preferably in the range which passes a U.S. 325 mesh sieve screen and more preferably is of the range normally produced in the conventional micronizing of a solid. In general, and within practical limits, the smaller the average diameter of the filler particles, the smoother is the surface of the resulting mold or impression. Preferred filling components are at least one of the oxides, sulfates and carbonates of the alkaline earths of Group II of the Periodic Table of the Elements. Refractory oxides of the metals of Groups III and IV, for example alumina K silica are also satisfactory. Calcium carbonate is most preferred. The filling component should be anhydrous or substantially so, that is, should contain little or no water whether loosely bound water or of water of hydration.

The Pacifying Component

The pacifying component is required to protect the binding component from deleterious effects which may be caused by trace amounts of water or acidic material or acidic sites which may be present in the filling material and lubricant component. The lower ($C_1$–$C_4$) tetra alkyl orthosilicates are especially suitable for and are contemplated for use as the pacifier component. Tetra ethyl orthosilicate is preferred. The amount of the pacifying component desirably used varies depending upon the trace water and the like present in the lubricating and filling components. Usually, a satisfactory amount is in the range 0.4 to 1.6 parts (weight), preferably 0.6 to 1.4, per 100 parts (weight) of the filling component.

The Binding Component

The binding component may vary widely depending upon the viscosity, setting time and the like characteristics desired for the composition herein. In general liquid and semi-liquid (paste-like) base compounds conventially employed to produce silicone rubbers by the introduction of a suitable catalyst into the material are satisfactory for use herein. The composition herein is of a putty-like, hand workable consistency. To obtain this consistency, and depending upon the individual properties of the components used, the relative amounts of the constituents are varied within the aforedescribed ranges. Thus, where a paste-like binding material is used, a relatively larger amount of the lubricating component and a relatively smaller amount of the filler is used. Where the binding component is of a low viscosity, on the other hand, less of the lubricating component and more of the filler are used.

Silicone rubber base compound materials (silicone rubber precursors) which under ambient conditions set up after addition of a curing catalyst to form a firm, flexible silicone rubber are, in general, suitable for use herein and such use is contemplated. Representative binding materials suitable for use herein, include RTV-11, a product of the General Electric Co. and Dow 3110, a product of the Dow Corning Co., and the like RTV-silicone rubber precursors. As discussed above, the amount of binding material relative to the filling component varies. In general, a satisfactory amount, per 100 parts (weight) of the filler, is in the range from about 4 to 12, preferably 6 to 10, parts.

The Catalyst

A wide range of catalysts are suitable for use in initiating the setting of the composition herein. These, in general, are the catalysts conventionally used in catalysing the polymerization of silicone rubber precursors. Representative catalysts include dibutyltindilaurate and stannous octoate and the like silicone rubber curing catalysts. These are normally available as commercial preparations varying in effectivity as to curing rate. A simple routine test establishes the relative amount desirably used. Control with a given catalyst is effected by increasing or decreasing the relative amount of catalyst added to the composition. Because of normal variations in catalyst effectivities depending upon the supplier, shelf life and other factors but one or two of the above-mentioned tests with timing thereof will provide the needed information with respect to amount to be used and the time available for applying the composition as desired. The following examples are for the further illustration but not the limitation of the invention.

EXAMPLE 1

The composition of the invention is especially suitable for use in repairing broken dentures. A serious problem encountered in such repair is the difficulty by conventional methods of maintaining the exact configuration of the original denture. In using the composition herein a portion thereof, after the hand kneading in of the catalyst is hand formed on a surface of which an impression is desired. Holding the broken denture together and in alignment, the repairman presses the putty onto the desired surface by hand, then waits for the brief period required to complete the initial set, i.e., 2–5 minutes. Thereafter, the broken denture is removed from the set, which is a perfect mold of the original unbroken denture. The parts of the broken denture in the area of the break are then ground down around the break in a manner which will provide a strong bonding for the separated pieces upon the filling of the void volume produced by the grinding with acrylic or epoxy denture material as desired. The pieces of the broken denture are then re-inserted into the mold and the required acrylic or epoxy bonding and repair composition is introduced to fill this void volume and thus to reconstitute the original denture. Whether or not there are undercut areas in the denture, its removal from and introduction back into the mold thus prepared is readily and easily effected without need for intermediate pasting materials, paper, foils or the like or for the chipping away of adhering plaster or stone as is often necessary in a conventional repair job. Thus the dimensional stability and the reproducibility of surface details by the setting of the composition of the invention provides a new and effective method for repairing broken dentures.

EXAMPLE 2

The composition herein provides a means for obtaining true bite or pallate registrations, for example for use in the manufacture of dentures. Again, a setting composition is obtained by hand kneading a satisfactory amount of catalyst into about two tablespoons of the catalyst-free composition. When the hand feel of the setting material indicates that the viscosity of the mix has reached a desirable stage, usually takes from one-half to 3 minutes to reach this stage, then a one-half to three-quarter inch diameter roll of the setting composition is formed into a cylindrical horseshoe and placed onto the occlusal and incisal surfaces of all lower teeth. The patient is then guided into the desired occlusal relationship, making certain that sufficient of the setting composition covers the lingual surfaces of all teeth, to ensure adequate bulk.

While the patient maintains the desired bite relationship, the setting composition is molded onto all facial surfaces with firm but gentle pressure. Concurrently, the patient presses the composition toward the lingual surfaces with his tongue.

When the set of the composition is completed, the resulting bite registration (impression) is removed, washed and air dried. Using a sharp knife or scalpel, the entire facial wall of the bite registration is trimmed off. This cut should be near the center of the occlusal table posteriorly and just lingual to the incisal edge, anteriorly. Finally all interproximal and lingual excess material is removed by trimming. The resulting "bite lock" is then ready for use with impressions or casts of the upper and lower teeth in the preparation of a set of dentures with full assurance that the occlusal relationship of the arches is correct.

EXAMPLE 3

The composition herein may be used effectively in combination with wax impressions and stone or plaster. It does not adhere to any of these materials. Thus in the relining of a denture a fresh temporary impression of the denture wearer's pallate may be adapted to the denture while it is in position inside the oral cavity. The impression is made using a wash material, for example soft acrylic washes. In the relining procedure the temporary lining has been removed and replaced with plastic, or acrylic resin and, of course, this substitute material must exactly duplicate the wash material for the production of a properly fitting denture. To this end, sufficient of the present composition to make a reverse impression of the wash material is converted to a setting material by hand kneading catalyst into it as described above. The setting material is then kneaded and/or pressed into intimate contact with the wash material and the plastic of the denture which holds the teeth in place. Next, when the composition has set, a cap of plaster or stone forming material is placed on top of the cast (set) composition and the whole assembly is inverted and placed on a steel base or jig before the plaster has set. Using a suitable foil or separator paper, a plaster cast (The reverse side of the temporary impression or liner does not have the strict requirement for faithful reproduction because it faces the void section of the oral cavity. Hence plaster is an adequate and convenient molding material.) is made of the reverse to the side of the wash liner of which the setting composition was used to reproduce the surface area. Before this upper plaster has hardened, it, too, is backed by a steel jig. Both jigs are mountable to a rigid frame whereby the whole assembly may be maintained in a fixed position.

The impression material (wash material) is next removed from the denture, and replaced with new acrylic or epoxy or the like, denture material. The metal jig is then closed to its original predetermined fixed position and the whole assembly is placed in an air-pressured chamber or put where the new plastic is cured. The use of the present composition in the above relining process is advantageous relative conventional processing in many respects, including (1) removal of the relined denture from the molding components is readily achieved without sticking problems, or subsequent chipping or grinding or the like, (2) the new liner contains none of the porosity normally encountered where stone is used rather than the present composition and (3) the accuracy and fidelity to detail of the new liner to the wash-impression is markedly improved over that for a new liner produced using plaster or stone in place of the present setting composition.

Processes

Repairs:

Referring to the drawings, specifically FIG. 2, a new technique for rapid repair of broken dentures is possible with this new putty, as now will be described in reference thereto. First, the broken dentures are glued together to restore them to a unitary structure. While such gluing is not adequate to return the dentures actual service, it is strong enough that the new putty 10 can be hand formed on to the pallate of denture 11, as shown in FIG. 2.

Once the catalyst has cured the putty, it is resilient enough that it can be removed from the glued dentures even though there are undercuts or the like in the resulting impression (mold). Subsequently the glued dentures are physically broken apart along the crack and the areas on each side thereof ground out or routed to a V-ed shape to provide room for new acrylic.

After the crack area has been enlarged the two pieces of the denture are replaced in the cured putty impression, thereby bringing them into exact position correspondence. At this time a liquid and powdered acrylic mixture is poured into the enlarged crack area and allowed to cure.

Curing of the mixture in the enlarged crack area can be enhanced by placing the dentures while still in the putty in a pressure pot operating at 15 p.s.i. and up to 240° F.

The putty impression separates easily from the repaired dentures and the technique is at least 10 times faster than using dental stone, without the usual problem experienced when the stone is chipped away from the repaired dentures when using the conventional processes.

Relines:

A new technique for cold cure relines is illustrated in FIGS. 1 through 3. Basically the roof portion of the pallate area 12 of someone's dentures 11 is relieved and then returned to their oral cavity with a wash material on the pallate area 12. This wash material forms a layer between the roof of the person's mouth and the denture that is extremely accurate in relationship to the contours of the mouth. After the wash is set up (formed) the new putty can be applied, as shown in FIG. 2, directly on top of the wash material.

When the putty has set up, the resulting combination is placed in a jig 13 whose upper half 14 and lower half 15 have conventional guides so they can be reassembled in an exact spacial relationship. Conventional dental stone 16 is placed between the upper half 14 of the jig and the teeth of the denture 11 and also open face of the putty and bottom half 15 of the jig (see FIG. 3). With the stone set up the jig is disassembled since the pallate area 12 will easily separate from the putty impression because of the latter's special non-sticky characteristics. Of course the teeth will remain invested in the dental stone at this time and the wash can be removed from the pallate area 12. Once this is accomplished the jig is reassembled with an excess of liquic acrylic between the pallate area and the putty impression. The putty is flexible enough that any excess acrylic automatically vents or flashes without the necessity of spillways and the like. However the putty's resiliency is such it always re-establishes its initial configuration after this occurs. The feature eliminates the time-consuming multiple packing steps necessary in conventional processes to achieve the right amount of acrylic to accomplish the reline.

Of course after the jig is reassembled the unit can be placed in a pressure pot operating at 15 psi and up to 240° F. to effect the final cure. After the final cure, the unit is disassembled and the newly relined area separates easily from the putty impression even though there may be undercuts in the denture surfaces in the pallate area 12. The teeth then are freed from the stone to complete the job.

A tremendous advantage is achieved over using conventional processes stone since the jig, when using the putty, can be easily separated after the cure. Further, if voids occur in the reline area one need add more acrylic and repeat the last few steps of the process. Obviously this cannot be done with stone because its surfaces are destroyed when the jig is separated.

Flasking Dentures:

The new putty also allows the utilization of a new process for flasking dentures, which allows a second flasking to be accomplished if the first one fails due to voids, etc.

In practicing this invention a pre-formed wax denture model 20 (see FIG. 4) with plastic teeth 21 set therein is positioned on soft dental stone 22 in surround by plaster 23 in the bottom half 24 of a flask 25. This stone conforms with the inner pallate area 26 of the wax denture model 20 (see FIG. 5) and hardens. Thereafter, the new putty 10 is hand formed over the projecting teeth 21 of the wax denture model, as well as the remaining exposed surfaces, as partially shown in FIG. 4. Because the putty is in a sense flowable, it can be readily hand worked to the exposed surfaces of the model 20 without disturbing its integrity. Once the putty sets-up the top half 27 of the flask is assembled with soft stone or backing plaster 28 so that the cured putty 10 with the wax model partially invested is suitably backed.

Thereafter, the wax of the model is boiled out leaving the plastic teeth 22 retained in the cured putty 10. In this process the resulting cavity is completely filled with liquid acrylic and then the flask 25 is assembled with pins (not shown) in guide holes 29 ensuring the same position correspondence between the two halves of the flask as when the wax model was invested therein. Initially the flask is closed with a 1/16" gap between its two halves to allow the excess acrylic to flow out of the cavity; thereafter the flask is forced closed while the acrylic is still liquid.

Subsequently, the flask can be placed in a pressure pot, as hereinbefore described. Once the cure of the acrylic is complete, the flask is easily separated due to the resilience of the putty which allows the plastic teeth to readily separate therefrom. Thereafter the pallate area 26 can be pried free of the backing stone 22. Since the surfaces in the flask are preserved, new teeth can be placed in the apertures in the putty and the latter steps of the process repeated to form a duplicate denture.

It should be appreciated that the new putty could be used for the pallate area 26 in place of stone 22, since once the putty cures, another batch of uncured putty will not stick to the cured putty. This would be desirable where the pallate area has undercuts making the release of the finished denture from the stone extremely difficult. In this latter technique, the putty would be hand-formed to the pallate area 26 in the same manner as in the case of the reline process described above.

We claim:

1. A method of repairing dentures comprising the steps of:
   (1) gluing a broken denture together along its break to restore it to its original integral configuration;
   (2) mixing a moldable, settable putty with a catalyst, said putty being a silicone type,
   (3) gently forcing a portion of said putty under pressure onto a surface of said glued broken denture so it conforms to and extends across said break, thereafter allowing said putty to set-up,
   (4) removing said broken denture from the resulting impression in said putty,
   (5) separating said denture along said break and removing denture material on either side thereof;
   (6) replacing said denture in the impression in said putty; and
   (7) subsequently adding settable plastic material to the area of said break to bond pieces of said denture together as a unitary, serviceable denture.

2. A method of relining denture which contain a wash material on the roof pallate surface comprising the steps of:
   (1) mixing a moldable settable putty with a catalyst, said putty being a silicone type;
   (2) gently forcing a portion of said putty under pressure onto the surface of the wash material disposed on a denture with teeth in a sufficient amount to cover it with at least a layer of ¼ of an inch, and allowing said putty to set-up thereafter;
   (3) placing said putty and denture in a dowelled two-part jig and setting the teeth of the denture and said putty with plaster-like material respectively in opposite parts of said jig and allowing said plaster-like material to harden,
   (4) subsequently separating said jig,
   (5) removing said wash material from the surface of said denture and
   (6) reassembling said jig with a settable liquid plastic material between said denture and said putty in sufficient amount to fill the cavity left by removal of said wash material and allowing said plastic material to set-up and bond to said denture thereby effecting a reline thereof.

* * * * *